US005741886A

United States Patent [19]

Stockel et al.

[11] Patent Number: 5,741,886
[45] Date of Patent: Apr. 21, 1998

[54] END-CAPPED POLYMERIC BIGUANIDES

[76] Inventors: Richard F. Stockel, 475 Rolling Hills Rd., Bridgewater, N.J. 08807; Murray Jelling, 21 Spring Hill Rd., Roslyn Heights, N.Y. 11577

[21] Appl. No.: 530,704

[22] Filed: Sep. 19, 1995

[51] Int. Cl.$^6$ .................................................. C08G 73/00
[52] U.S. Cl. .................... 528/422; 528/425; 523/122; 523/169; 524/612
[58] Field of Search ...................... 528/422, 425; 523/122, 169; 524/612

[56] References Cited

U.S. PATENT DOCUMENTS

| | | | |
|---|---|---|---|
| 2,643,232 | 6/1953 | Rose et al. | 260/2 |
| 3,428,576 | 2/1969 | Dickinson et al. | 260/2 |
| 4,403,078 | 9/1983 | McCoy et al. | 525/504 |
| 4,558,159 | 12/1985 | McCoy et al. | 564/233 |
| 4,891,423 | 1/1990 | Stockel | 528/422 |

FOREIGN PATENT DOCUMENTS

| | | | |
|---|---|---|---|
| 702268 | 1/1954 | United Kingdom | 2/3 |
| 1152243 | 5/1969 | United Kingdom | C08G 33/02 |
| 1167249 | 10/1969 | United Kingdom | C08G 33/02 |
| 1531717 | 11/1978 | United Kingdom | C08G 73/00 |

*Primary Examiner*—Duc Truong

[57] ABSTRACT

Linear, polymeric biguanides or salts thereof wherein the polymeric chain is terminated at the cyanoguanidine end group by a $C_2$–$C_{90}$ primary or secondary amine which is optionally substituted with a functionality such as fluoride, chloride, bromide, iodide, nitro, hydroxyl, ether, sulfide, disulfide, sulfoxide or sulfone. The polymeric biguanides have a high level of biocidal activity accompanied by a low level of toxicity to host organisms and are therefore useful in bactericidal, algicidal and fungicidal compositions, especially in ophthalmic compositions.

17 Claims, No Drawings

5,741,886

END-CAPPED POLYMERIC BIGUANIDES

FIELD OF THE INVENTION

The invention relates to linear polymeric biguanides (also referred to herein as "polybiguanides") or salts thereof wherein the polymeric chain moiety is wholly or substantially wholly terminated (i.e. "mono end-capped") at its cyanoguanidine end group with a primary or secondary monoamine which optionally contains functionalities such as fluoride, chloride, bromide, iodide, nitro, hydroxyl, ether, sulfide, disulfide, sulfoxide or sulfone. The invention also relates to biocidal compositions, e.g. algicidal, bactericidal and fungicidal compositions, such as ophthalmic compositions, containing such polybiguanides or salts thereof as the active ingredient in such compositions.

BACKGROUND OF THE INVENTION

Polymeric biguanides (and their salts thereof) having structures differing from those of the present invention are well known in the prior art. The prior art poly-biguanides have structures wherein the cyanoguanidine end group is not terminated (i.e. not mono end-capped) and are stated to have biocidal, i.e. antibacterial and antifungal properties. Representative prior art patents comprise U.K. patents 702,268; 1,432,345; and 1,531,717. PCT Application WO86/02001 describes polyhexamethylene biguanide salts which are stated to be useful as preservatives for cosmetics.

U.S. Pat. Nos. 4,403,078 and 4,558,159 describe polybiguanides of the polyether and polyoxyalkylene-diamine types which are stated to be useful as surfactants and epoxy resin curing agents.

U.S. Pat. No. 4,891,423 describes a very useful class of linear, polymeric biguanides (and water-soluble salts thereof) containing polymethylene radicals and/or polyoxyalkylene radicals offering the unique capability of control of the desired hydrophilic-lipophilic balance in order to achieve maximum penetration of the cellular structure of the pathogenic organism.

Although many of the prior art polybiguanide compositions, especially those of the '423 patent, are quite useful in biocidal compositions, they nevertheless fail to achieve the high level and rate of kill of a broad spectrum of pathogenic organisms while having the low level of toxicity to the host organism as do the polymeric biguanides of the present invention.

DETAILS OF THE INVENTION

The present invention comprises a linear polymeric biguanide or a salt thereof wherein the polymeric chain is wholly or substantially wholly terminated at its cyanoguanidine end group by a primary or secondary monoamine containing about 2–90 carbon atoms. The monoamine is optionally substituted with a functionality selected from the group consisting of fluoride, chloride, bromide, iodide, nitro, hydroxyl, ether, sulfide, disulfide, sulfoxide and sulfone.

Preferably, the monoamine is an aliphatic, cycloaliphatic, heterocyclic, aryl, aralkyl, alkaryl or polyether monoamine containing oxyalkylene groups such as oxyethylene and/or oxypropylene. More preferably, the monoamine is a primary amine containing 3–70 carbon atoms, e.g. n-dodecylamine, 2-aminothiazole, 2-amino-benzothiazole, polyoxyethylene monoamine, polyoxypropylene monoamine or polyoxy (ethylene/propylene) monoamine.

Desirably, the polybiguanide is one which, in the form of its free base, comprises recurring units of the general formula:

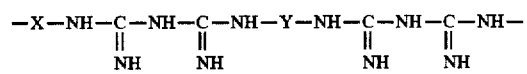

wherein X and Y are the same or different organic radical bridging groups. Suitable examples of the organic radicals represented by X and Y include $C_2$–$C_{140}$ aliphatic, cycloaliphatic, heterocyclic, aryl, alkaryl, aralkyl and oxyalkylene radicals.

Preferably, X is a polyoxyalkylene radical and Y is a polyalkylene radical optionally interrupted by oxygen, nitrogen or sulfur atoms, or by saturated or unsaturated cyclic nuclei; for the purposes of the present invention, the oxygen, nitrogen or sulfur atoms may be present as —O—, —N—, —NH—, —S—, —S—S—, —SO—, —SO$_2$—, and the like.

Desirably, Y is a $C_4$–$C_{16}$ polymethylene radical and X is a polyoxyalkylene radical derived from the amines selected from the group consisting of:

(a) amine-terminated polypropylene glycols having the structure:

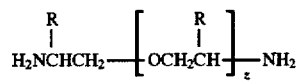

wherein R is H or $CH_3$ and z has a value of about 1 to 68;

(b) polyether diamines having the structure:

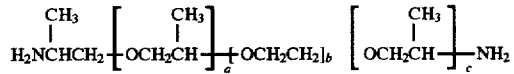

wherein b has a value of about 8.5 to about 131.5 and the value of a+c is about 2.5;

(c) urea condensates of amine-terminated polypropylene glycols having the structure:

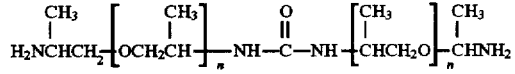

wherein n has a value of about 2.6;

(d) amine-terminated polyethylene glycols having the structure:

wherein m has a value of about 1 to 4; and (e) amine-terminated polypropylene glycols having the structure:

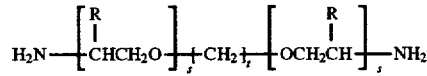

wherein s has a value of 1 to about 10; t has a value of 2 to about 8; and R is hydrogen or methyl.

Particularly preferred are those polybiguanides wherein the polyoxyalkylene radical is derived from amine-terminated polyethylene glycols having the structure:

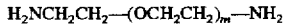

wherein m has a value of about 1 to 4.

The polybiguanides of the present invention are especially useful as the active ingredient in fungicidal or bactericidal compositions, since such compositions will exhibit a high level and rate of kill for pathogens while concurrently resulting in a low level of toxicity. The polybiguanides of the present invention are effective biocidal substances, e.g. at concentrations of 1.0–1.000 ppm (0.0001–0.1 wt. %), they have been found to be effective in standard evaluations against bacteria, fungi, algae, yeasts, spores, etc. such as *S. aureus, E. coli, P. aeruginosa, A. niger* and *C. albicans*. Standard dermal and oral tests with rats and skin and eye evaluations with rabbits indicated that the polybiguanides of the invention possess low cytotoxicity.

The polybiguanides of the invention are useful for recreational waters such as swimming pools and spas; process waters; preservatives for protective coatings such as paints; personal products such as cosmetics and toiletries; industrial products for metal working, oil drilling, etc.; crop protection; hospital products such as for surgical scrubs, preoperative equipment, skin disinfection and area sanitizing.

Typically, the fungicidal or bactericidal composition will contain a polybiguanide of the invention in the form of a salt together with a carrier substance therefor. The polybiguanide may be present in an amount of about 10 to 40 wt. %, based on the weight of the composition. Preferred salts comprise chloride, bromide, iodide, acetate, citrate, glycolate, gluconate, sulphate or tartrate.

Suitable carriers comprise liquid or solid diluents. In the case of the diluent being water, wetting agents, dispersing agents, emulsifying agents may also be advantageously incorporated in the compositions. Suitable examples of solid carriers include kaolin, bentonite, kieselguhr, dolomite, calcium carbonate, talc, gypsum, diatomaceous earth, fuller's earth and the like.

One of the principal biocidal uses of the polymeric biguanides of the present invention is for ophthalmic compositions, i.e. compositions useful for various types of contact lenses (e.g. hard, soft, extended wear, semipermeable, etc.). Such ophthalmic uses will include incorporation of the polybiguanides in various forms, e.g. wetting solutions, enzyme cleaners, sterile saline solutions, preservatives for ophthalmological preparations, disinfectant solutions, etc.

Ophthalmic compositions containing the polybiguanides of the present invention may be prepared in the form of concentrates or diluted solutions. When prepared as concentrates, the composition will typically contain 4 to 80 wt. %, preferably 10 to 30 wt. % of the polybiguanide. In the form of a dilute solution which is intended for contact lens purposes, the concentrate is usually diluted (e.g. with distilled water, saline, etc.) such that the final concentration of the polybiguanide in the dilute solution will be in the range of about 0.0001 to 0.1 wt. %, based on the weight of the dilute solution.

For ophthalmic purposes, it is preferred that the aqueous solution containing a polybiguanide of the present invention be isotonic or substantially isotonic with tear fluid. Such solution will typically have a pH of 5.0 to 8.0, preferably 6.5 to 7.5. If desired, the solution may be buffered (e.g. with boric acid, sodium borate, potassium tetraborate, potassium metaborate, etc.) to maintain the pH in the desired range. If desired, adjuvants may be incorporated in the ophthalmic solution, e.g. thickening agents such as polyvinyl alcohol, carboxymethyl cellulose, hydroxyethylcellulose, and the like; nonionic surfactants such as the polyethylene glycols and their esters of fatty acids such as coconut, polysorbate, etc.

Ophthalmic solutions containing a polybiguanide of the present invention may also contain ophthalmic drugs, in which case the polybiguanide acts as a preservative for the drug solution. Suitable ophthalmic drugs include myotic drugs such as pilocarpine; mydriatic drugs; anti-infective agents such as chloramphenicol; anti-inflammatory drugs such as steroids, etc.

The end-capped polybiguanides of the present invention are readily prepared by a variety of multi-step processes wherein the linear, polymeric biguanide intermediates are prepared and isolated and thereafter reacted with the monoamine end-group modifier.

In one type of process, the polybiguanide intermediate is prepared by reacting equimolar amounts of the desired diamine (the diamine may be one diamine or a mixture of diamines, as desired) and one mole of the desired biscyanoguanidine compound or a mixture of the desired biscyanoguanidine compounds in the presence of hydrochloric acid. The components are conveniently brought into reaction by heating them alone or in a neutral solvent, e.g. water, alcohols, glycols, glycol ethers, etc. at a temperature of 90°–190° C., preferably 100°–170° C., for a period of 2–24 hours, preferably 2–12 hours.

Another method for preparing the polybiguanide intermediate involves the reaction of one mole of sodium dicyanamide and 0.5 mole of the desired diamine (one diamine or a mixture of diamines, as desired) in the form of its dihydrochloride salt. The reaction mixture is heated as is or in one of the solvents mentioned above at a temperature of 90°–190° C., preferably 100°–170° C., for 2–12 hours. The resultant 0.5 mole of the biscyanoguanidine compound is separated from the sodium chloride and thereafter reacted with 0.5 mole of the same or different diamine dihydrochloride as is or in one of the solvents mentioned above at a temperature of 90°–190° C., preferably 100°–170° C., for a period of 2–24 hours, preferably 2–12 hours.

The processes mentioned above for preparation of the linear, polymeric biguanide intermediates are well known in the prior art, e.g. see U.S. Pat. Nos. 2,643,232, 3,428,576 and 4,891,423 and British Patents 702,268, 1,152,243 and 1,167,249.

The end-capped polybiguanides of the invention are readily prepared by the reaction of the desired polybiguanide with the desired primary or secondary monoamine. In this manner, only the cyanoguanidine end group is modified (i.e. "end-capped").

This type of modification of principally polycondensation polymers is documented in the literature and is known to those skilled in polymer chemistry.

One method of preparation is set forth in Example 1, although it should be understood that this is not the only method by which the end-capped polybiguanides of the present invention may be prepared. It should be understood that other prior art methods may be used to prepare such polybiguanides without departing from the spirit of the present invention.

The following examples serve to illustrate the invention; unless otherwise indicated, all parts are by weight.

EXAMPLE 1

A preferred method for preparing the end-capped polybiguanides of the present invention is as follows. The compound known as 1,6-di($N^3$-cyano-$N^1$-guanidino)hexane was prepared in accordance with Example 1 of U.S. Pat. No. 4,537,746. 25.0 g (0.1 m) of this biscyanoguanidine was combined with 14.8 g (0.1 m) of triethyleneglycoldiamine and 20 g of 37 wt. % hydrochloric acid (0.2 m) in a flask containing 20 ml distilled water. The reaction mixture was stirred and heated in an oil bath to drive off the water. Heating at 160°–165° C. with stirring was continued for about 3 hours. Upon cooling, a white, glassy polymer was obtained in nearly quantitative yield.

The polymer was then "mono end-capped" as follows: The polybiguanide from above was reheated to about 160° C. and 1.87 g (0.01 m) of n-dodecylamine were added with stirring for about 2 hours resulting in the mono end-capped polybiguanide.

EXAMPLE 2

Following the procedure set forth in Example 1, a series of mono end-capped polybiguanides were prepared using the monoamines and the diamines (0.1 mole) indicated in the Table set forth below:

TABLE

| Monoamine | Monoamine Mol. Wt. | g/mole | Diamine |
|---|---|---|---|
| n-octylamine | 129.2 | 0.646/0.005 | Jeffamine ® 148[a] |
| n-octadecylamine | 269.5 | 2.695/0.01 | HMDA[b] |
| 2-aminothiazole | 100.1 | 1.001/0.01 | Jeffamine ® 148[a] |
| 2-aminobenzo-thiazole | 150.2 | 1.502/0.01 | Jeffamine ® 148[a] |
| 2-amino-5-bromo-pyrimidine | 174.1 | 3.482/0.02 | Jeffamine ® 148[a] |
| 3-amino-1,2,4-triazine | 96.1 | 0.768/0.008 | Jeffamine ® 148[a] |
| 3-amino-1,2,4-triazole | 84.08 | 0.630/0.0075 | Jeffamine ® 148[a] |
| 2-(4-thiazoyl)-benzimidazole | 201.2 | 2.012/0.01 | Jeffamine ® 148[a] |
| p-chlorobenzyl-amine | 141.6 | 1.416/0.01 | HMDA[b] |
| 2,4-dichloro-benzylamine | 176.05 | 1.760/0.01 | HMDA[b] |
| Surfonamine ™ MNPA[c] | 1000 | 10.00/0.01 | Jeffamine ® 148[a] |
| Jeffamine ® M-2005[d] | 2005 | 20.05/0.01 | Jeffamine ® 148[a] |

[a]Jeffamine ® 148 is a diamine with an approximate molecular weight of 148 and having the structure: $H_2N$—$CH_2CH_2$—O—$CH_2CH_2$—O—$CH_2CH_2$—$NH_2$
[b]HMDA is an acronym for hexamethylenediamine
[c]Surfonamine ™ MNPA is a surface-active polyether amine having the structure $C_9H_{19}$— —($OCH_2CH_2$)$_{15}$—[$OCH_2CH(CH_3)$]$_2$—$NH_2$
[d]Jeffamine ® M-2005 is a polyoxyalkyleneamine prepared by reaction of a monohydric alcohol initiator having the structure $CH_3OCH_2CH_2O$— with propylene oxide and ethylene oxide in a PO/EO molar ratio of 32/2, followed by conversion of the resulting terminal hydroxyl group to an amine.

It is to be understood that the foregoing examples are illustrative only and that other means and techniques can be employed without departing from the true scope of the invention as defined in the following claims.

What is claimed is:

1. A linear polymeric biguanide or a salt thereof wherein the polymeric chain is wholly or substantially wholly terminated at its cyanoguanidine end group by a primary or secondary monoamine containing 2–90 carbon atoms, said monoamine being optionally substituted with a functionality selected from the group consisting of fluoride, chloride, bromide, iodide, nitro, hydroxyl, ether, sulfide, disulfide, sulfoxide and sulfone, said polymeric biguanide, in the form of its free base, comprising recurring units of the general formula:

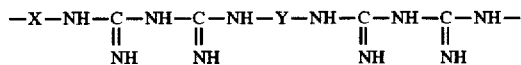

wherein X and Y are the same or different organic radical bridging groups.

2. The polymeric biguanide of claim 1 wherein the monoamine is selected from the group consisting of aliphatic, cycloaliphatic, heterocyclic, aryl, aralkyl, alkaryl and polyether monoamines containing oxyalkylene groups.

3. The polymeric biguanide of claim 2 wherein the monoamine is a primary amine containing 3–70 carbon atoms.

4. The polymeric biguanide of claim 3 wherein the monoamine is unsubstituted.

5. The polymeric biguanide of claim 4 wherein the monoamine is selected from the group consisting of n-dodecylamine, 2-aminothiazole, 2-aminobenzotriazole, polyoxyethylene monoamine, polyoxypropylene monoamine and polyoxy(ethylene/propylene) monoamine.

6. The polymeric biguanide of claim 1 wherein the organic radicals represented by X and Y are the same or different $C_2$–$C_{140}$ aliphatic, cycloaliphatic, heterocyclic, aryl, alkaryl, aralkyl or oxyalkylene radicals.

7. The polymeric biguanide of claim 6 wherein X is a polyoxyalkylene radical and Y is a polyalkylene radical optionally interrupted by nitrogen, oxygen or sulfur atoms, or by saturated or unsaturated cyclic nuclei.

8. The polymeric biguanide of claim 7 wherein Y is a $C_4$–$C_{16}$ polymethylene radical.

9. The polymeric biguanide of claim 8 wherein X is a polyoxyalkylene radical derived from the amines selected from the group consisting of:

(a) amine-terminated polypropylene glycols having the structure:

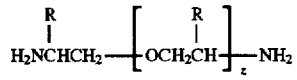

wherein R is H or $CH_3$ and z has a value of about 1 to 68;

(b) polyether diamines having the structure:

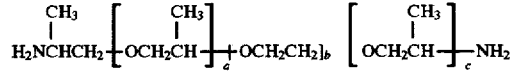

wherein b has a value of about 8.5 to about 131.5 and the value of a+c is about 2.5;

(c) urea condensates of amine-terminated polypropylene glycols having the structure:

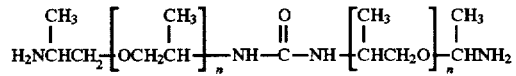

wherein n has a value of about 2.6;

(d) amine-terminated polyethylene glycols having the structure:

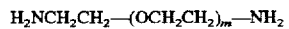

wherein m has a value of about 1 to 4; and (e) amine-terminated polypropylene glycols having the structure:

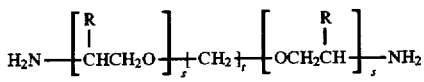

wherein s has a value of 1 to about 10; t has a value of 2 to about 8; and R is hydrogen or methyl.

10. The polymeric biguanide of claim 9 wherein the polyoxyalkylene radical is derived from amine-terminated polyethylene glycols having the structure:

wherein m has a value of about 1 to 4.

11. The polymeric biguanide of claim 1 wherein the salt comprises a chloride, bromide, iodide, acetate, citrate, glycolate, gluconate, sulphate or tartrate.

12. A bactericidal composition comprising as the active ingredient, the polymeric biguanide of claim 1, together with a carrier substance therefor.

13. The composition of claim 12 wherein the polymeric biguanide is present in an amount of about 10 to 40 wt. %, based on the weight of the composition.

14. A fungicidal composition comprising as the active ingredient, the polymeric biguanide of claim 1, together with a carrier substance therefor.

15. The composition of claim 1 wherein the polymeric biguanide is present in an amount of about 10 to 40 wt. %, based on the weight of the composition.

16. An ophthalmic composition comprising an aqueous solution of the polymeric biguanide of claim 1.

17. The composition of claim 16 wherein the polymeric biguanide is present in an amount of about 0.0001 to 0.1 wt. %, based on the weight of the composition.

* * * * *